US009731037B2

United States Patent
Nijsen et al.

(10) Patent No.: US 9,731,037 B2
(45) Date of Patent: Aug. 15, 2017

(54) SCANNING SUSPENSION COMPRISING A PARTICLE WITH A DIAMETER OF AT LEAST 1 MICROMETER

(71) Applicants: Universitair Medisch Centrum Utrecht, Utrecht (NL); Universiteit Utrecht Holding B.V., Utrecht (NL)

(72) Inventors: Johannes Franciscus Wilhelmus Nijsen, Utrecht (NL); Alfred Dirk Van Het Schip, Nieuwegein (NL); Bernard Antoni Zonnenberg, Maarssen (NL)

(73) Assignees: Universitair Medisch Centrum Utrecht (NL); Universiteit Utrecht Holding B.V. (NL)

( * ) Notice: Subject to any disclaimer, the term of this patent is extended or adjusted under 35 U.S.C. 154(b) by 95 days.

(21) Appl. No.: 14/108,567

(22) Filed: Dec. 17, 2013

(65) Prior Publication Data

US 2014/0227177 A1 Aug. 14, 2014

Related U.S. Application Data

(60) Division of application No. 11/025,360, filed on Dec. 29, 2004, now Pat. No. 8,632,751, which is a continuation-in-part of application No. PCT/NL03/00485, filed on Jul. 2, 2003.

(30) Foreign Application Priority Data

Jul. 2, 2002 (EP) .................................... 02077626

(51) Int. Cl.
| | | |
|---|---|---|
| *A61K 9/00* | (2006.01) | |
| *A61K 51/12* | (2006.01) | |
| *A61K 49/18* | (2006.01) | |
| *A61K 33/24* | (2006.01) | |
| *A61K 49/00* | (2006.01) | |

(52) U.S. Cl.
CPC .......... *A61K 51/1282* (2013.01); *A61K 33/24* (2013.01); *A61K 49/00* (2013.01); *A61K 49/1821* (2013.01); *A61K 51/1255* (2013.01)

(58) Field of Classification Search
CPC ........ A61K 33/00; A61K 33/24; A61K 49/00; A61K 49/1821; A61K 51/00; A61K 51/1217; A61K 51/1241; A61K 51/1255; A61K 51/1282; A61K 51/04; A61K 51/06; A61K 51/065; A61K 51/12; A61K 51/1244; A61K 51/1251; B82Y 5/00
USPC .... 424/1.11, 1.29, 1.37, 1.65, 9.1, 9.3, 9.32, 424/400, 489, 617; 977/773
See application file for complete search history.

(56) References Cited

U.S. PATENT DOCUMENTS

| | | | |
|---|---|---|---|
| 4,863,715 A | 9/1989 | Jacobsen et al. | |
| 4,985,233 A | 1/1991 | Klaveness et al. | |
| 5,099,505 A | 3/1992 | Seppi et al. | |
| 5,213,788 A | 5/1993 | Ranney | |
| 5,512,268 A | 4/1996 | Grinstaff et al. | |
| 6,373,068 B1 * | 4/2002 | Nijsen .................. | A61K 41/009 250/432 PD |
| 7,572,448 B2 * | 8/2009 | Thorpe ................ | A61K 39/395 424/130.1 |
| 8,632,751 B2 * | 1/2014 | Nijsen ................ | A61K 49/1821 424/1.11 |
| 8,691,280 B2 * | 4/2014 | Nijsen .................. | A61K 41/009 424/1.29 |
| 9,334,298 B2 * | 5/2016 | Bult ....................... | A61K 49/08 |

FOREIGN PATENT DOCUMENTS

| | | |
|---|---|---|
| DE | 19958586 A1 | 6/2001 |
| JP | 10-328319 A | 12/1998 |
| JP | 2001-327514 A | 11/2001 |
| JP | 5-502400 B2 | 5/2014 |
| WO | 92/17214 A2 | 10/1992 |
| WO | 93/10440 A1 | 5/1993 |
| WO | WO 97/01304 * | 1/1997 |
| WO | 2004/004786 A1 | 1/2004 |

OTHER PUBLICATIONS

Frantisek (Nuclear Physics Methods and Accelerators in Biology and Medicine, Jun. 27-Jul. 11, 2001, pp. 83-98).*
Hall et al (Radiobiology for the Radiologist, 2006, Lippincott Williams & Wilkins, Sixth Edition, 7 total pages).*
Mumper et al, Journal of Nuclear Medicine, 1991, vol. 32, pp. 2139-2143.*
J.F.W. Nijsen et al., "Holmium-166 poly lactic acid microspheres applicable for intra-arterial radionuclide therapy of hepatic malignancies: effects of preparation and neutron activation techniques," European Journal of Nuclear Medicine, vol. 26, No. 7, Jul. 1999, pp. 699-704.

(Continued)

*Primary Examiner* — D L Jones
(74) *Attorney, Agent, or Firm* — Banner & Witcoff, Ltd.

(57) ABSTRACT

The invention provides a scanning suspension comprising a particle which is capable of at least in part disturbing a magnetic field, wherein said particle comprises a diameter of at least 1 μm, and use thereof for obtaining a scanning image. Preferably, said particle comprises holmium and a composition capable of essentially maintaining its structure during irradiation. A particle of the invention is suitable for preparing a kit of parts, comprising a diagnostic and a therapeutic composition which both comprise particles of the invention with essentially the same chemical structure, wherein said therapeutic composition is more radioactive than said diagnostic composition. Said kit of parts is especially suitable for treatment of a tumor. First, the distribution of a particle of the invention within an individual can be determined with a scanning image obtained with said scanning composition. Subsequently, a radioactive therapeutic composition can be administered, wherein a suitable dose of said therapeutic composition is derived from said scanning image.

9 Claims, 11 Drawing Sheets

(56) References Cited

OTHER PUBLICATIONS

S. Fossheim et al., "Lanthanide-Based Susceptibility Contrast Agents: Assessment of the Magnetic Properties," Magn Reson Med 1996; 35(2): 201-206.
H. Kooijman et al., "Diaquatris(pentane-2,4-dionato-O,O')holmium(III) monohydrate and diaquatris(pentane-2,4-dionato-O,O')-holmium(III) 4-hydroxypentan-2-one solvate dihydrate," Acta Crystallographica C 2000; 56(Pt 2): 156-158; ISSN: 0108-2701.
J.G. Kidd et al., "A Transplantable Rabbit Carcinoma Originating in a Virus-Induced Papilloma and Containing the Virus in Masked or Altered Form," J. Exp. Med 71 (469), 813-837, 1940; Ref Type: Journal (Full).
R.J.J. van Es et al., "The VX2 carcinoma in the rabbit auricle as an experimental model for intra-arterial embolization of head and neck squamous cell carcinoma with dextran microspheres," Lab Anim 1999; 33(2): 175-184.
M. J. Herba et al., "Hepatic Malignancies: Improved Treatment with Intraarterial Y-901," Radiology 1988: 169(2): 311-314.
R.M. Weisskoff et al., "Microscopic Susceptibility Variation and Transverse Relaxation: Theory and Experiment," Magn Reson Med 1994; 31(6): 601-610.
D.A. Yablonskiy et al., "Theory of NMR Signal Behavior in Magnetically Inhomogeneous Tissues: The Static Dephasing Regime," Magn Reson Med 1994; 32(6): 749-763.
R.A. Fox et al., "Dose Distribution Following Selective Internal Radiation Therapy," Int. J. Radiation Oncology Biol. Phys. vol. 21, (1991), pp. 463-467.
E.D. Yorke et al., "Can Current Models Explain the Lack of Liver Complications in Y-90 Microsphere Therapy," Clincal Cancer Research, vol. 5, Oct. 1999 (Suppl.), 3024s-3030s.
Jun. 28, 2013—(US) Final Office Action—U.S. Appl. No. 11/025,360.
Dec. 13, 2013—(US) Non Final Office Action—U.S. Appl. No. 11/025,360.
T.R. Golub et al., "Molecular Classification of Cancer: Class Discovery and Class Prediction by Gene Expression Monitoring," Science, vol. 286, Oct. 15, 1999, pp. 531-537, www.sciencemag.org.
Mar. 22, 2010—(AU) Office Action—Application No. 2003281270.
Jun. 25, 2010—(AU) Office Action—Application No. 2003281270.
J.H. Turner et al., "166Ho-microsphere liver radiotherapy: a preclinical SPECT dosimetry study in the pig," Nuclear Medicine Communications (1994) 15; 545-553.
R.J. Mumper et al., "Neutron-Activated Holmium-166-Poly (L-Lactic Acid) Microspheres: A Potential Agent for the Internal Radiatin Therapy of Hepatic Tumors," Journal Nucl Med. 1991, vol. 32, No. 2139-2143.
J.F.W. Nijsen et al., "Characterization of poly(L-lactic acid) microspheres loaded with homium acetylacetonate," . Biomaterials 2001, No. 22, 3073-3081.
J.F.W. Nijsen et al., "Radioactive homium loaded poly(L-lactic acid) microsheres for treatment of hepatic malignancies: efficacy in rabbits," Chapter 7, Thesis, 2001, pp. 109-122.
J.F.W. Nijsen et al., "Targeting of liver tumour in rats by selective delivery of holmium-166 loaded microspheres: a biodistribution study," European Journal of Nuclear Medicine, Thesis, 2001, Chapter 6, pp. 95-108.
Nov. 13, 2009—(US) Final Office Action—U.S. Appl. No. 11/025,360.
Feb. 20, 2009—(US) Non Final Office Action—U.S. Appl. No. 11/025,360.
Melichar Frantisek, "Preparation of 166 Ho labeled compounds for endoradiotherapy and skin cancer therapy," Nuclear Physics Methods and Accelerators in Biology and Medicine, pp. 83-98.
J.F.W. Nijsen et al., "Influence of neutron irradiation on holmium acetylacetonate loaded poly(L-lactic acid) microspheres," Biomaterials, (2002), vol. 23, pp. 1831-1839.
A.G. Webb et al., "Sonochemically Produced Fluorocarbon Microspheres: A New Class of Magnetic Resonance Imaging Agent," J. Magnetic Resonance Imaging, 6(4): 675-683 (1996).

* cited by examiner

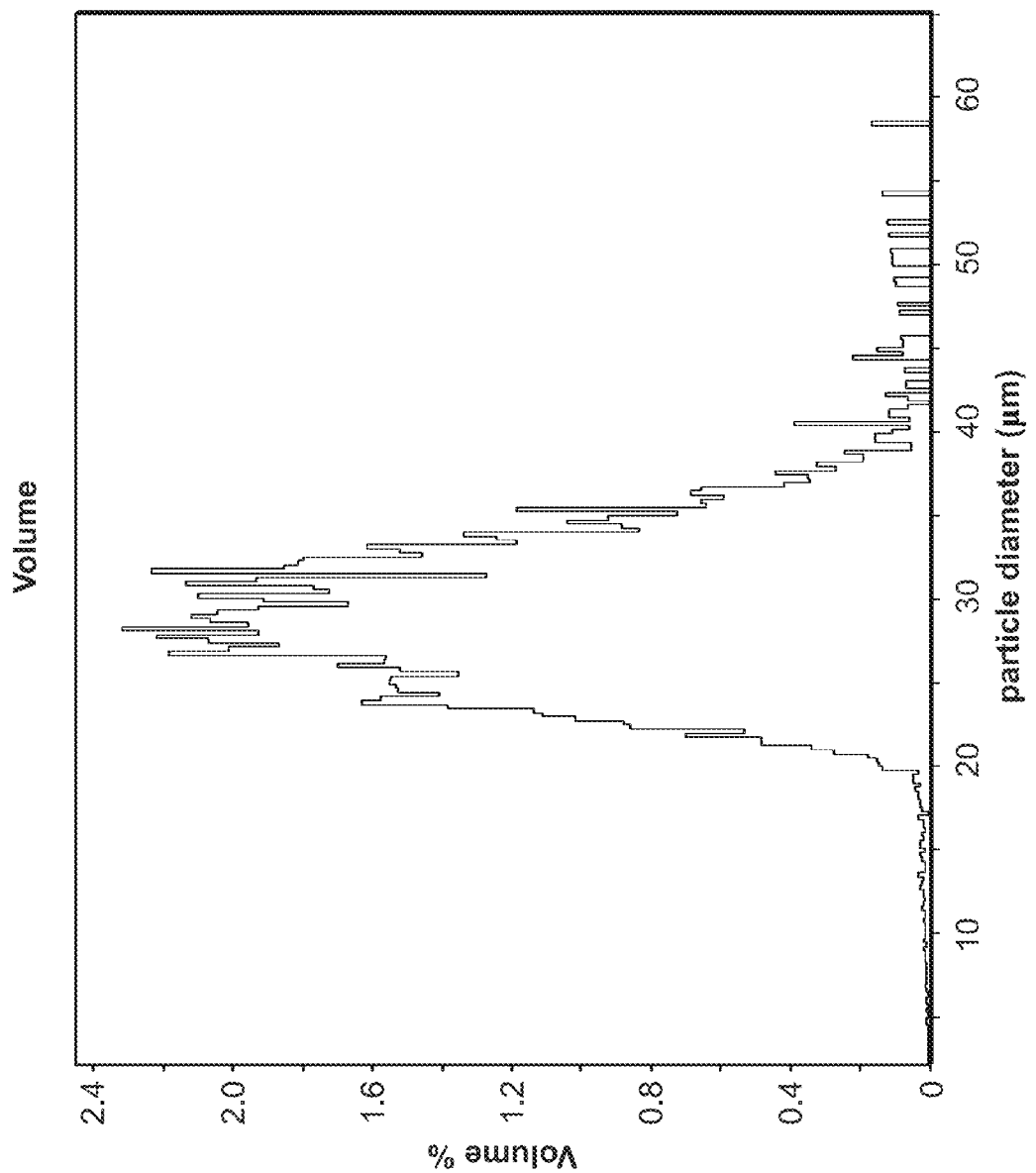

SCANNING SUSPENSION COMPRISING A PARTICLE WITH A DIAMETER OF AT LEAST 1 MICROMETER

RELATED APPLICATIONS

This application is a divisional of U.S. application Ser. No. 11/025,360 filed Dec. 29, 2004, which is a continuation of International application PCT/NL2003/000485, filed Jul. 2, 2003, which claims the benefit of EP patent application number 02077626.6 filed Jul. 2, 2002, all of which are hereby incorporated herein by reference in their entireties.

BACKGROUND

The invention relates to the field of medicine. More specifically, the invention relates to the field of diagnostics and radiotherapy.

Reliable, detailed diagnostics is often a key prerequisite for efficient treatment of a disorder. Especially disorders which display a significant different pattern in each individual patient involve the need for very careful and accurate diagnosis. Such disorders for instance comprise tumour-related diseases. If a patient has been found to suffer from a tumour, it is important to obtain reliable insight into the status of the disease. For instance the growth and position of the tumour should be established, and it should be determined whether there are metastases in other parts of the body, etc. Additionally, adequate information about targeting of a drug to a tumour can increase a treatment efficacy.

Many scanning techniques are known, such as magnetic resonance imaging (MRI) which provide information of the internal status of an individual. A contrast agent is often used in order to be capable of obtaining a scanning image. For instance ferrite particles and gadolinium-DTPA (diethylaminetriaminepentaacetic acid) complexes are often used in contrast agents for MR scanning. This way, a good impression can be obtained of internal disorders, like the presence of (a) tumour(s).

After diagnosis, a treatment is often started involving administration of a pharmaceutical composition to a patient. It is often important to monitor the status of a patient during treatment as well. For instance the course of a treatment and targeting of a drug can be monitored, as well as possible side effects which may imply a need for terminating, or temporarily interrupting, a certain treatment.

Sometimes local treatment in only a specific part of the body is preferred. For instance, tumour growth can sometimes be counteracted by internal radiotherapy comprising administration of radioactive particles to an individual. If said radioactive particles accumulate inside and/or around the tumour, specific local treatment is possible. However, to prevent radiation-induced gastritis and/or radiation pneumonitis, patients with significant shunting to the gastroduodenum and the lungs must be excluded from therapy. Therefore, the exact distribution of the radioactive particles is determined by firstly administering a tracer dose comprising said radioactive particles. This involves extra exposure of radioactivity, both for the patient and the medical staff, which is unwanted. Furthermore, some kind of radioactive particles, such as radioactive yttrium, can hardly be detected with a gamma camera. If such yttrium particles are to be used for therapy, other radioactive particles (for example: technetium labelled albumin particles) which can be detected with a gamma camera and which are expected to target and distribute approximately similar as said yttrium particles are administered before treatment. A distribution of said other radioactive particles is then determined. Because said distribution of said other radioactive particles is considered to be approximately similar to a distribution of yttrium, it can approximately be estimated whether significant shunting of yttrium to the gastroduodenum and/or the lungs will occur.

It is thus very complicated to determine how such particles should be used, and what the distribution pattern will be. These problems cannot be solved with current non-radioactive scanning techniques, because the distribution of MRI contrast agents is not the same as the distribution of radioactive therapeutic compounds.

After the radioactive therapeutic compound has become non- (or barely) radioactive, its distribution cannot be followed anymore. This is inconvenient, because it would be desirable to monitor how said compound is removed from the body. Information about the biodistribution of said compound gives an indication about the course of a disease and/or treatment, and about the status of a patient.

SUMMARY

It is an object of the present invention to provide an alternative scanning suspension. A scanning suspension of the invention can be used for existing applications. New applications with a suspension of the invention are also herewith provided.

The invention provides a scanning suspension comprising a particle which is capable of at least in part disturbing a magnetic field, wherein said particle comprises a diameter of at least 1 μm. Said particle can be detected by a non-radioactive scanning method such as MRI. Preferably said scanning suspension comprises an MRI scanning suspension. More preferably, said particle comprises holmium.

A use of a particle which is capable of at least in part disturbing a magnetic field for the preparation of a scanning suspension, wherein said particle comprises a diameter of at least 1 μm is also herewith provided. Methods to generate a scanning suspension, such as an MRI scanning suspension, are known in the art and need no further description here. With a scanning suspension of the invention a scanning image can be obtained. Thus, the invention provides a use of a scanning suspension comprising a particle which is capable of at least in part disturbing a magnetic field for obtaining a scanning image, wherein said particle comprises a diameter of at least 1 μm. Preferably said scanning image comprises an MR scanning image. In this application the meaning of the word suspension has to be understood as at least including dispersions.

BRIEF DESCRIPTION OF THE DRAWINGS

FIG. 1a-b. a) Scanning electron micrograph of holmium loaded PLLA microspheres. b) Volume weight distribution of sieved microspheres. The used microspheres for the experiments had a mean diameter of 30 μm and 96% of the volume of the particles had a diameter between 20 and 40 μm.

DETAILED DESCRIPTION OF CERTAIN EXEMPLARY EMBODIMENTS

Figure 1A:
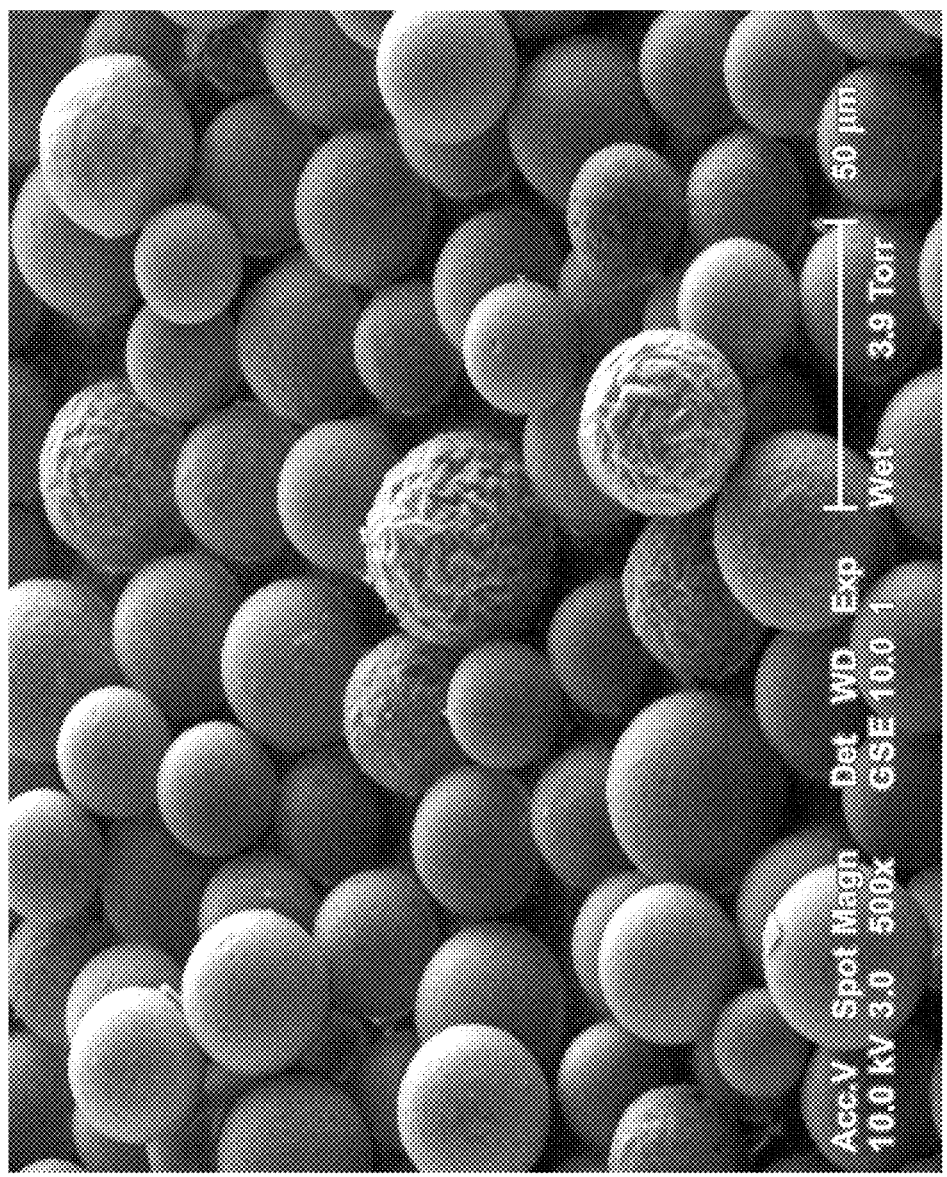

A scanning suspension of the invention is suitable for determining a flowing behaviour of a particle. Since a scanning suspension of the invention comprises a particle of at least 1 µm, it can simulate the flowing pattern of such relatively large particles. A use of a scanning suspension comprising a particle with a diameter of at least 1 µm which is capable of at least in part disturbing a magnetic field for determining the flowing behaviour of said particle is therefore also herewith provided.

A scanning suspension of the invention, comprising a particle with a diameter of at least 1 µm which is capable of at least in part disturbing a magnetic field, is also very suitable for detecting a site of angiogenesis. A site of angiogenesis can be detected by determining the flowing behaviour of said particle. Preferably said particle comprises holmium. The size of said particle can be chosen such to enable said particle to get stuck in a blood vessel. Typically said size comprises a diameter of about 3-5 µm. A site of angiogenesis can be detected after administration of said particles to an individual. At a site with many (developing) blood vessels, the concentration of stuck particles will be high compared to other parts of the body. Detection of said site is thus possible, for instance by MRI scanning. One embodiment of the invention therefore provides a use of the invention for detecting a site of angiogenesis.

A scanning suspension of the invention is also very suitable for detecting a tumour. This can for instance be performed by determining the flowing behaviour of a particle of the invention, and/or by detecting a site of angiogenesis, with a use according to the invention. A presence of a tumour often involves a site of angiogenesis, because a tumour often needs much oxygen and nutrients for a high metabolism rate. Therefore new blood vessels are generated around said tumour. Hence, a site of angiogenesis can be indicative for a presence of a tumour. Said tumour can be detected without the need of using radioactive material. Alternatively, particles with low radioactivity can be used. After a tumour has been detected, said tumour can be treated with a therapeutic composition comprising the same kind of particles as said scanning suspension. In said therapeutic composition, however, said particles are preferably rendered (more) radioactive. Despite the difference in radioactivity, the particles of said diagnostic composition and the particles of said therapeutic composition are chemically the same. Therefore, the distribution of the radioactive particles of said therapeutic composition can be adequately predicted by determining the distribution of the particles of a scanning suspension of the invention. The size of the particles are preferably sufficiently large to avoid an equal distribution throughout the whole body. In one embodiment said therapeutic composition comprises a particle of the invention which is provided with at least one therapeutically active compound, for instance capable of treating a tumour.

The invention therefore provides a use of the invention for detecting a tumour. Preferably, said tumour comprises a liver metastasis.

In a preferred embodiment a use of the invention is provided wherein said scanning suspension comprises an MRI scanning suspension.

In yet another preferred embodiment a use of the invention is provided wherein said particle comprises a diameter sufficiently large to enable said particle to be stuck within a tumour. Such particle is very suitable for detecting a tumour. More preferably, said particle is at least in part capable of flowing through non-tumorous vessels. Such particle can stick in a tumour vessel while less sticking in normal vessels. This is possible because of the fact that tumour vessels are mostly somewhat smaller and more irregularly formed than normal vessels. This way, tumour tissue can be very adequately distinguished from normal tissue, because a higher concentration of particles of the invention will be present in tumour tissue. Said particle of the invention preferably comprises a diameter of approximately 1-10 µm. More preferably, such particle comprises a diameter of about 2-8 µm, most preferably about 3-5 µm.

To distinguish tumorous from non-tumorous tissue, it is preferred to firstly administer a scanning suspension of the invention comprising particles, which are capable of at least in part disturbing a magnetic field, with a small diameter, for instance about 3 µm. Then it can be determined whether those particles stick within tumorous vessels. If they do not stick within said tumorous vessels yet (the size of tumorous vessels will vary to some extent) one can administer a second dose of scanning suspension comprising particles of the invention with a somewhat larger diameter, for instance about 4 µm. If these particles still do not stick within said tumorous vessels, a scanning suspension comprising particles of the invention with an even larger diameter can be administered, etc. This way the minimal diameter can be determined allowing a particle of the invention to stick within a certain tumour while still being capable of flowing through non-tumorous vessels. Said minimal diameter can vary between different tumours, and between different patients. Said minimal diameter is often between 3-5 µm. This way it is possible to detect a tumour with a scanning suspension of the invention comprising particles of the invention which stick within tumorous vessels while still being capable of flowing through non-tumorous vessels.

In one aspect the invention provides a method for detecting a tumour, comprising
   administering to an individual a scanning suspension comprising a particle which is capable of at least in part disturbing a magnetic field, wherein said particle comprises a diameter of at least 1 µm;
   obtaining a scanning image; and
   determining whether said image reveals the presence of a tumour.

Preferably, said particle comprises a diameter of approximately 3-5 µm. As outlined above, a method of the invention can comprise administering to an individual different scanning suspensions, comprising particles of the invention with different size. Preferably, each different scanning suspension is administered separately, with a time interval between administration of each suspension. Alternatively, different scanning suspensions can be administered simultaneously, or shortly after one another.

In another preferred embodiment, a particle of the invention comprises a diameter of approximately 15-200 µm, more specifically 15-100 µm, even more specifically 20-100 µm, more preferably 20 to 50 or 80-100 µm. A particle of this size is very suitable for radiotherapeutic purposes. Said particle comprises a diameter sufficiently large to enable said particle to be lodged within arterioles. Hence, said particle is suitable for embolizing a blood vessel, preferably embolizing an arteriole. A tumour can be deprived from blood, and therefore be deprived from oxygen and nutrients, by lodging at least one blood vessel near said tumour with a particle of the invention. This is possible because of the fact that a tumour receives an increased blood flow as compared to normal tissue. Therefore an increased amount of particles of the invention will lodge in and around a tumour as compared to normal tissue. For instance, tumours in the liver receive their blood for the greater part from the hepatic artery while normal liver tissue receives its blood mainly from the portal vein. This results in an increased amount of particles of the invention in and around the tumour after administration of said particles in the hepatic artery. Said particles can for instance be administrated to the hepatic artery with a catheter. Embolizing a blood vessel with a particle of the invention is also particularly suitable for treating a tumour present in the throat and/or head of an individual. The invention thus provides a use of a particle which is capable of at least in part disturbing a magnetic field, wherein said particle comprises a diameter of approximately 20-100 µm, for embolizing a blood vessel. In using relatively large particles, for example between 50-200 µm, for example, embolisation of tumours, bone cancer and tumours due to Tuber Sclerosis is possible. This latter decease results in very large benign kidney tumours which are very painful and may lead to rupture of blood vessels and death of a patient. Using particles of said size according to the invention embolisation of the vessels leading to said tumour may lead to retardation of tumour growth and prevent excessive exposure to radiation for patients and staff.

In yet another embodiment, a particle of the invention is administered to a particle or complex of interest. Preferably said particle or complex of interest comprises a particle or complex with a desired function which it can perform within an organism. More preferably, said particle or complex of interest comprises an organelle or cell of an organism. Most preferably, said particle or complex of interest comprises a liposome or a white blood cell. After administration of a particle of the invention to a particle or complex of interest, said particle or complex of interest can be detected by a scanning method such as MRI. This way a presence and/or migration of said particle or complex of interest can be detected. For instance, a liposome is useful for delivering a nucleic acid of interest to a suitable site for gene therapy. If such liposome has been provided with a particle of the invention it can be determined where said liposome is present inside an organism. It can then be estimated whether a nucleic acid of interest is delivered to a desired site. As another example, after administration of a particle of the invention to a white blood cell, migration of said white blood cell to a site of inflammation, or to a tumour, can be detected using a scanning method such as MRI. The invention thus provides a use of a particle of the invention for detecting a presence and/or migration of a particle or complex of interest.

In one embodiment, a suspension comprising a particle which is capable of at least in part disturbing a magnetic field, wherein said particle comprises a diameter of at least 1 µm is used for the preparation of a kit of parts. Said suspension can be used as such as a diagnostic composition. Alternatively, said suspension can be used for the preparation of a diagnostic composition. Preferably said suspension is essentially non-radioactive. Another aliquot of said suspension can be made (more) radioactive. Said other aliquot is very useful for radiotherapy. Such radioactive suspension of the invention can thus be used as a therapeutic composition. Additionally, a composition comprising such radioactive suspension of the invention can be used as a therapeutic composition. In one embodiment a radioactive therapeutic composition of the invention comprises a particle of the invention which is provided with at least one therapeutically active compound, for instance capable of treating a tumour. Said therapeutic composition is for instance capable of treating a tumour simultaneously by radiotherapy and with a therapeutic action of said compound. In an alternative embodiment a non-radioactive therapeutic composition of the invention comprises a particle of the invention which is provided with at least one therapeutically active compound, for instance capable of treating a tumour. Said therapeutic composition is capable of treating a tumour by a therapeutic action of said compound. Of course, a particle of the invention can be provided with any therapeutic compound. Such particle is suitable for treatment of any disease against which said therapeutic compound can perform its therapeutic action.

Said diagnostic composition and said therapeutic composition are suitable for the preparation of a kit of parts.

The invention provides a kit of parts comprising a diagnostic composition and a therapeutic composition, said diagnostic composition and said therapeutic composition comprising particles of the invention with essentially the same chemical structure, said therapeutic composition being more radioactive than said diagnostic composition. Preferably, said diagnostic composition is essentially non-radioactive. In one embodiment, said particles comprise holmium. Said diagnostic composition can be used to determine a distribution of said particles inside an individual. This can for instance be determined by MRI. Hence, there is now no more need for a radioactive tracer dose. This is both beneficial for the patient and for the medical staff. No special precautionary measures have to be taken against (too much) exposure to radioactive radiation. Moreover, if a radioactive tracer dose is used, a distribution pattern has to be determined within limited time, before radioactivity has decayed. However, if a diagnostic composition of the invention is essentially non-radioactive, a distribution pattern of said particles does not have to be determined within limited time. Said distribution can now be determined during the whole time that said particles are present within an individual. Hence, more time is available now for determining a distribution pattern.

Subsequently, it can be decided whether said individual is capable of undergoing radioactive therapy with said therapeutic composition. This is for instance dependent on the degree of shunting of said particles to the lungs and the gastrointestinal tract. Also, the optimal amount of radioactive therapeutic composition to be administered to said individual can be determined, by interpretation of the obtained distribution pattern of said diagnostic composition. It can be determined how many particles accumulate in a tumour, if they are distributed inside said tumour, etc. Because said (more radioactive) particles of said therapeutic composition are chemically the same as said particles of said diagnostic composition, the distribution of said therapeutic composition will be the same as the distribution of said diagnostic composition in said individual.

In one embodiment a kit of parts is provided wherein said diagnostic composition comprises a suspension of the invention.

In yet another embodiment a kit of parts is provided comprising a diagnostic composition and a therapeutic composition, said diagnostic composition and said therapeutic composition comprising particles with essentially the same chemical structure which are capable of at least in part disturbing a magnetic field, wherein said particles comprise a diameter of at least 1 µm, wherein said therapeutic composition comprises a particle of the invention which is provided with at least one therapeutically active compound. The distribution of said therapeutic composition can be followed over time using a scanning method such as MRI. In one embodiment said therapeutic composition is essentially non-radioactive.

In one embodiment, a particle of the invention comprises a microsphere. Preferably, said microsphere comprises holmium.

Biodegradable poly (L-lactic acid) microspheres (PLLA-MS) were manufactured in a glass beaker with four baffles, Holmiumacetylacetonate (Ho-AcAc) complex (10 g) and PLLA (6 g) were added to continuously stirred 186 g chloroform. PVA was dissolved in continuously stirred water of 40° C. and poured into the glass beaker after cooling. The solutions and the beaker were kept at 25° C. The chloroform solution was added to the PVA solution and continuously stirred (500 rpm) until the chloroform was completely evaporated. To remove residual PVA and unincorporated Ho-AcAc, the formed microspheres were washed sequentially with water, 0.1 N HCl and water. The microspheres were graded and collected according to size on stainless steel sieves of 20 and 50 micrometer (20 micrometer sieve, S/Steel, NEN 2560, Endecotts, London; 50 micrometer sieve, S/Steel, ASIM E 11-87; B.V. metaalgaasweverij, Twente, The Netherlands) under sprinkled water, and dried under nitrogen. Characterisation of non-irradiated and irradiated microspheres was carried out by SEM, laser particle size analysis and gamma-spectrometry of 166 Ho, after neutron activation of the 165 Ho incorporated in the PLLA-MS. For determination of PLLA molecular weight, microspheres were dissolved in chloroform and analysed by high-performance liquid chromatography (HPLC) using a gel permeation chromatography column (Shodex KD 800) from Showa Benco, Japan. Samples were irradiated individually and within 1 day, in order to create reactor conditions as closely comparable as possible. It appeared that well-defined irradiation conditions were necessary to produce therapeutic dosages of 166 Ho-PLLA-MS while maintaining there integrity and suitability for therapy. Non-irradiated 156 Ho-PLLA-MS show a smooth, spherical appearance. After irradiation in the PRS facility (neutron flux $5 \times 10^{13}$ $cm^{-2}.s^{-1}$) for 1 h in polyethylene vials, minor surface changes were seen with SEM, giving rise to small PLLA fragments. These led to a larger number of particles, <20 micrometer. While overall structural integrity was maintained in terms of form and size, the microspheres showed a minimal tendency towards aggregation; they could, however, be easily suspended in PBS and should be suitable for intra-arterial therapy.

The present inventor has developed holmium loaded poly(L-lactic acid) microspheres (also called herein "holmium microspheres"), which can be detected by MRI. These microspheres can be used to generate an essentially non-radioactive diagnostic composition. With this diagnostic composition, the flowing behaviour of a particle of the invention, a site of angiogenesis, the presence of one or more tumours, and/or the distribution of said composition inside and around a tumour can for instance be determined. Additionally, it can be estimated whether significant shunting to the gastroduodenum and the lungs occurs.

Once the distribution of said composition inside a patient is known, another sample of holmium loaded poly(L-lactc acid) microspheres can be rendered radioactive, for instance by neutron activation. These radioactive holmium microspheres can be used to generate a therapeutic composition. The distribution of said therapeutic composition inside said patient will be the same as the distribution of said diagnostic non- (or low-) radioactive composition, because said microspheres are chemically the same. Thus, from the acquired (MRI-)information about the distribution of the diagnostic composition the optimal amount of therapeutic composition can be determined.

Alternatively, the administered essentially non-radioactive microsphere can be made radioactive in vivo. This can for instance be done by neutron activation. However, it is possible that the administered amount of diagnostic composition appears not to be the optimal amount for the patient involved, since different patients can display different distribution patterns. Therefore, preferably an optimal amount of a radioactive therapeutic composition is administered after the distribution of said non-radioactive diagnostic composition is determined. It is also possible, in intervention MRI, to follow the administration and dosing of microspheres according to the present invention.

In terms of the invention, an individual means an animal, preferably a human.

By a particle of the invention is meant herein a particle which is capable of at least in part disturbing a magnetic field, wherein said particle comprises a diameter of at least 1 µm. Preferably said particle is paramagnetic, for instance comprising holmium, gadolinium and/or dysprosium. A particle of the invention has a different susceptibility to a magnetic field as compared to the environment. A particle of the invention for instance comprises a molecule bound to an element capable of at least in part disturbing a magnetic field. Said molecule may form a cave wherein said element is present. For instance, said particle comprises a microsphere. However, any particle comprising said element falls within the scope of a particle of the invention. A particle only containing said element also falls within the scope of a particle of the invention. Preferably said element comprises holmium. By a suspension of the invention is meant a suspension comprising a particle of the invention.

By a composition or a particle which is more radioactive than another composition or particle is meant that the amount of radioactivity per mole is higher. This amount of radioactivity is normally expressed in becquerel.

By essentially non-radioactive is meant that the radioactivity is essentially the same as the normal background values generally present.

In terms of the invention, chemically the same means that the chemical formula is essentially the same, or that a particle comprises an essentially similar shape while comprising essentially the same kind of sub-particle(s). Such sub-particle for instance comprises a particle of the invention. However, elements or compounds which are chemically the same may comprise different isotopes. A certain isotope of an element is considered to have essentially the same chemical properties compared to another isotope of the same compound.

By the expression "a particle with a diameter of 1 µm" is meant that a batch of said particles comprises particles with a mean value of approximately 1 µm. For instance, if said batch comprises microspheres, the size of each individual microsphere can vary between approximately 0.5 and 2 µm. The same applies for other diameter sizes described in this application.

By "treating a tumour" is meant herein that said tumour is counteracted. This can result in decreased growth of said tumour. In some cases growth can be stopped. Said tumour may be killed, although this is not necessarily the case.

The invention further provides a method for treating an individual suffering from a tumour, comprising:

administering to said individual a scanning suspension comprising a particle which is capable of at least in part disturbing a magnetic field;

obtaining a scanning image of said individual;

determining the distribution of said particle within said individual;

administering to said individual a therapeutic composition comprising said particle. Said particle in said therapeutic composition is more radioactive than said particle in said diagnostic composition, and/or is provided with at least one therapeutically active compound.

Preferably, said particle comprises holmium. More preferably, the optimal amount of said therapeutic composition is derived from the distribution of said particle of said scanning suspension. In one embodiment, said scanning suspension comprises a scanning suspension of the invention.

A method of the invention is particularly suitable for treatment of a liver tumour, for instance a liver metastasis.

Liver metastases frequently occur during the progression of various solid tumours, especially colorectal cancers, and are the cause of 25-50% of all cancer deaths. The median survival of patients with liver metastases ranges from 2-12 months depending on volume of the metastases and histology of the original tumour. Surgical resection is presently the only approach that offers patients with liver metastases substantial chance of cure. However this is an option for only 10-20% of the patients.

External beam radiotherapy in the treatment of hepatic malignancies is limited by the tolerance of the hepatic parenchyma, which can tolerate doses of only up to 30 Gy for whole liver irradiation; this treatment modality is therefore ineffective. With a method of the invention treatment of liver malignancies is improved.

A particularly useful mode of therapy is the use of intra-arterially injected radioactive particles of the invention of a size sufficient to lodge in endarterioles. The basis for such therapy is that tumours are usually rich in vasculature and that liver metastases are almost exclusively dependent on arterial blood supply. This contrasts with normal liver, which receives most of its flow from the portal vein. This selectivity can also be increased by the use of vasoactive drugs, which cause vasoconstriction of the normal liver arterioles, but to which tumour vessels, lacking smooth muscle, are insensitive. Of course, other kind of tumours can also be treated by lodging of a blood vessel by a particle of the invention.

In one embodiment, a method of the invention is provided wherein said particle comprises a microsphere, for instance a poly(L-lactic acid) microsphere.

Preferably, said particle comprises holmium.

For example, neutron activated radioactive holmium loaded poly(L-lactic acid) microspheres (Ho-PLLA-Ms) emit gamma rays which can be used for imaging with a gamma-camera and beta particles for treatment of a patient. Animal studies showed that these microspheres can be targeted to the tumour and that they can be easily imaged with a gamma camera. Since holmium is paramagnetic it can also be viewed by non-radioactive scanning methods such as MRI. It is therefore possible to image non-radioactive holmium loaded microspheres. Imaging of non-radioactive holmium loaded microspheres before treatment with radioactive microspheres results in a radiation reduction for the patient and medical personnel. In that case no special precautionary measures have to be taken against (too much) exposure to ionizing radiation, as has been explained above. Moreover, more time is now available for determining a distribution pattern. Said distribution can now be determined during the whole time that said particles are present within an individual, whereas a radioactive tracer dose should be detected before radioactivity has decayed.

Furthermore, the distribution of holmium loaded microspheres can be also followed over time.

In yet another embodiment the invention provides a method for obtaining a scanning image, comprising administering a scanning suspension to an individual and subsequently generating a scanning image of said individual, wherein said scanning suspension comprises a scanning suspension of the invention.

The following examples are meant to illustrate the present invention. They do not limit the scope of the invention in any way.

EXAMPLES

The purpose of this study was to investigate the possibility of measuring the biodistribution of holmium loaded microspheres with MRI. Measurements were done in phantoms, in ex-vivo rabbit livers and in rabbits. MR images of the rabbits were compared with gamma scintigraphic images.

Methods and Materials

Preparation of microspheres. Radioactive holmium loaded microspheres were prepared as previously described [14]. Briefly, holmium acetylacetonate [20] is incorporated into poly(L-lactic acid) by solvent evaporation, resulting in microspheres of 20-50 μm after sieving. Neutron activation of the microspheres was performed by irradiation for 1 h in the PRS facility of the high-flux nuclear reactor in Petten, The Netherlands. Prior to administration during the in-vivo and ex-vivo experiments the microspheres were sonicated for 10 min in an ultrasonic cleaner and suspended in Gelofusine® (Vifor Medical SA, Switzerland).

Phantoms. For preparation of the agar gel matrix dry agar powder (20 g; Life technologies GIBCO BRL, Paisley, Scotland) was mixed in cold deionized water (1000 g) with manganese(II) chloride tetrahydrate (900 mg; Merck, Darmstadt, Germany) The manganese-chloride was used to simulate liver NMR properties. Holmium or yttrium loaded poly(L-lactic acid) microspheres (Ho-PLLA-MS or Y-PLLA-MS) were suspended in the agar solution under stirring. The microspheres suspension and agar suspension were heated till 100° C. for 10 minutes resulting in transparent fluid gels. The gels were added in different proportions to each other which resulted in a rising Ho-PLLA-MS and Y-PLLA-MS concentration. The mixed gels were sonicated during cooling. Once cooled to room temperature, the gel is optically transparent with visible homogeneously distributed microspheres.

Rabbits. All experiments were performed in agreement with The Netherlands Experiments on Animals Act (1977) and the European Convention guidelines (86/609/EC). Approval was obtained from the University Animal Experiments Committee. The experiments were performed using four female pathogen-free New Zealand White inbred hsdlF rabbits of 3000-4000 g (Harlan, Horst, The Netherlands). The rabbits were housed individually in steel cages and provided daily with approximately 100 g "complete diet" pellets for rabbits. Water was provided ad libitum. The three tumour bearing rabbits were sacrificed after three or four weeks. The Rabbit without tumour was sacrificed direct after the SPECT and MRI images were taken.

Analgesia, sedation and euthanasia. Analgesia and sedation during laparatomies were achieved with 0.5 ml methadone (10 mg/ml; Veterinary Pharmacy, University of Utrecht, The Netherlands) and 0.5 ml Ventranquil® (acepromazine, 10 mg/ml; Sanofi Sante Animale Benelux BV, Maassluis, The Netherlands. Subsequently, the rabbits were anaesthetized by an intravenous injection of Hypnomidate® (2 mg/ml; B. Braun Melsungen AG, Melsungen, Germany) and $N_2O$ and halothane (Albic BV, Maassluis, The Netherlands) as inhalation anasteticum. Rabbits were sacrificed with 3 ml Euthesate (pentobarbital, 200 mg/ml; Apharmo b.v., Arnhem The Netherlands).

Tumour cells. The VX2 cell line [21] was obtained from the Department of Oral and Maxillofacial Surgery of the University Medical Center, Utrecht, The Netherlands [22]. The VX2 tumour was propagated by subcutaneous passage in the hip region of the rabbit. After the tumour was dissected small parts (2 mm in diameter) were chosen for implantation.

Tumour implantation. Tumour parts (two or three) were injected in the left lateral lobe with an Abbocath® 18G (Abbocath Ltd., Ireland). The injection wound was sealed with tissue glue (Histoacryl, B. Braun Melsungen AG, Melsungen, Germany). After approximately 12 days the first ultrasound investigation (HDI 3000 ATL, Entos™ CL10-5 transducer) was performed to check tumour growth.

Administration of the microspheres. When the tumour had reached a diameter of ≥20 mm, a second laparatomy was performed in order to administer the holmium loaded microspheres. The gastroduodenal artery was cannulated with an Abbocath® 24G (Abbott Ltd., Ireland). Back flow was checked with 0.1% methylene blue in 5% glucose. A preflushed administration system similar as described by Herba et al. [23] was connected to the Abbocath®. The suspended microspheres were administered and the syringe was measured for activity pre- and post injection, in order to calculate the injected dosage. The gastroduodenal artery was ligated or if possible sealed with tissue glue (Histoacryl, B. Braun Melsungen AG, Melsungen, Germany). MR images were taken before, three days after and 17 days after administration of the radioactive microspheres. SPECT images were taken three days after administration. In order to verify presence of microspheres liver was embedded in paraffin and histologically evaluated after staining with haematoxylin-eosin.

Ex-vivo liver. The liver was derived from a rabbit used in a terminal animal experiment. No extra rabbits were killed for performing these ex-vivo experiments. A needle was jabbed in the left ventricle of the heart and the right auricle was cut away. The rabbit was flushed with saline and heparine; 500 ml with 1 ml heparine (Leo Pharma BV, Weesp, 5000 IE/1 ML). The liver was removed and the hepatic artery was cannulated with a Abbocath® 24 G. Again the liver was flushed with saline and heparine via the hepatic artery. The livers were stored in saline by 5° C. during a maximum of 30 hours. The suspended microspheres were administered via the hepatic artery during the dynamic MR-imaging experiments.

Magnetic resonance imaging. All MR investigations were performed on a whole body system operating at 1.5 T (Gyroscan ACS-NT 15, Philips Medical Systems). The imaging protocol included $T_1$-weighted SE imaging and $T_2$-weighted SE imaging.

Scintigraphic imaging. After administration of the radioactive microspheres imaging of the total rabbit and the abdominal region was performed using a dual-head camera (Vertex-MCD, ADAC, Milpitas, Calif.). A planar and SPECT image was generated. SPECT acquisition involved a rotation of each detector of 180° with 32 stops at 30 s per stop.

Results

Microspheres Microspheres prepared by solvent evaporation resulted after sieving in 3-5 grams spherical particles with a diameter of 20-50 μm (FIG. 1) and a holmium content of 15-17% (w/w).

Figure 2A:
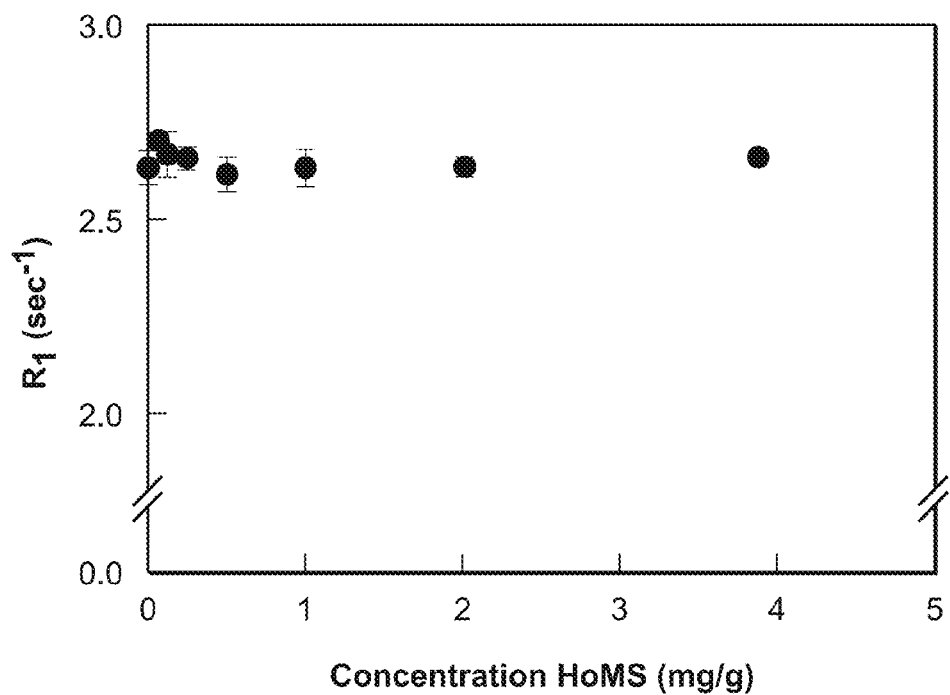
FIG. 2a-b. a) $R_1$ and b) $R_2$ versus HoMS concentration. The solid line is a least squares fit to the data points.
Figure 2B:
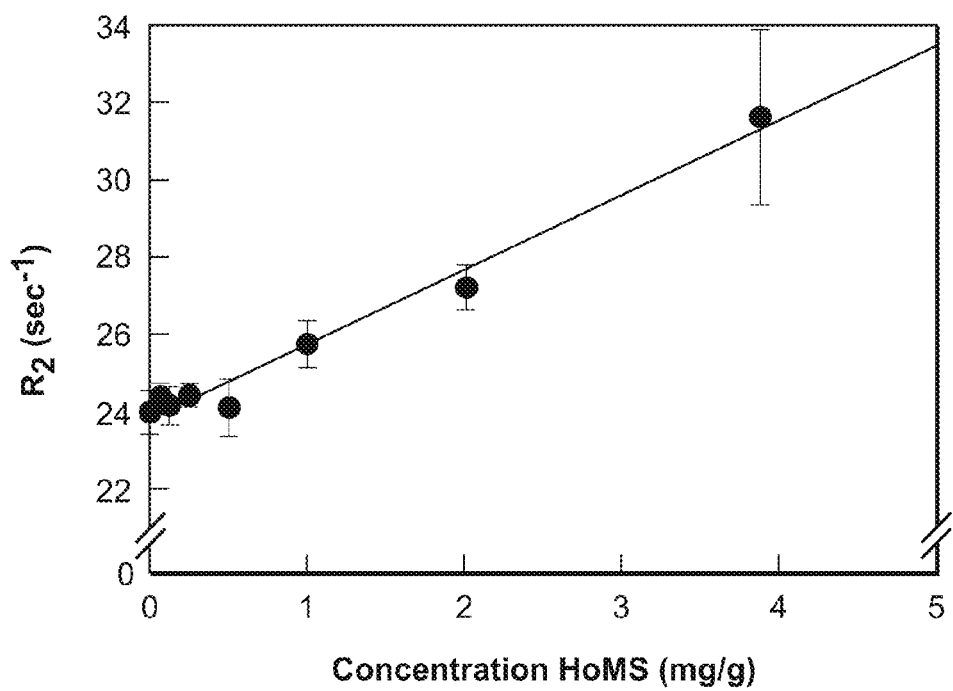
Figure 3:
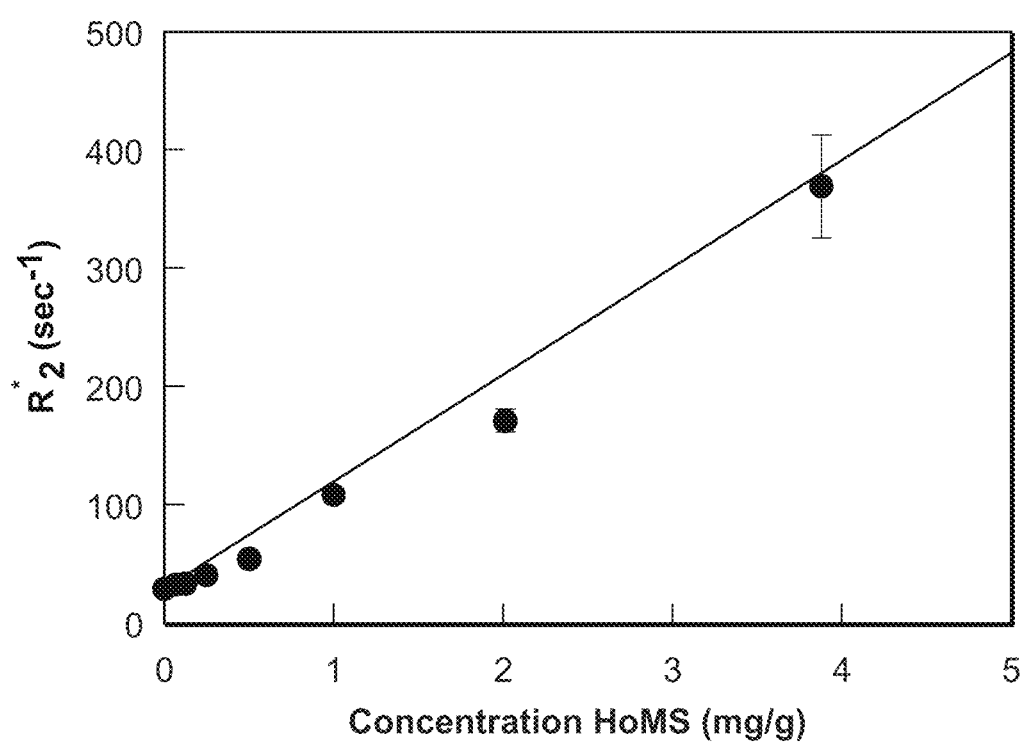
FIG. 3. $R_2^*$ versus HoMS concentration. The solid line represents the theoretical result in the static dephasing regime (Eq. 11 in Ref. 7) as calculated from the holmium content of the spheres.

Phantoms R1 and R2 as measured by the multi spin-echo with inversion recovery experiment were largely independent of the concentration of holmium microspheres, FIG. 2. The least squares fit suggests $\Delta R_2 = 1.93 \times [HoMS]$ s$^{-1}$, [HoMS] in mg/g. This is to be expected for stationary paramagnetic perturbers of this size, because the perturbing particles are large compared to the diffusion length of the protons [24]. FIG. 3 shows the $R_2^*$ dependence on HoMS concentration. The transverse relaxivity corresponds to that predicted for the static dephasing regime [25], where the susceptibility of the HoMS is calculated using the Curie law from the magnetic moment of uncoupled Ho ions (10.4 Bohr magnetons) and the Ho content of the microspheres.

Figure 4A:
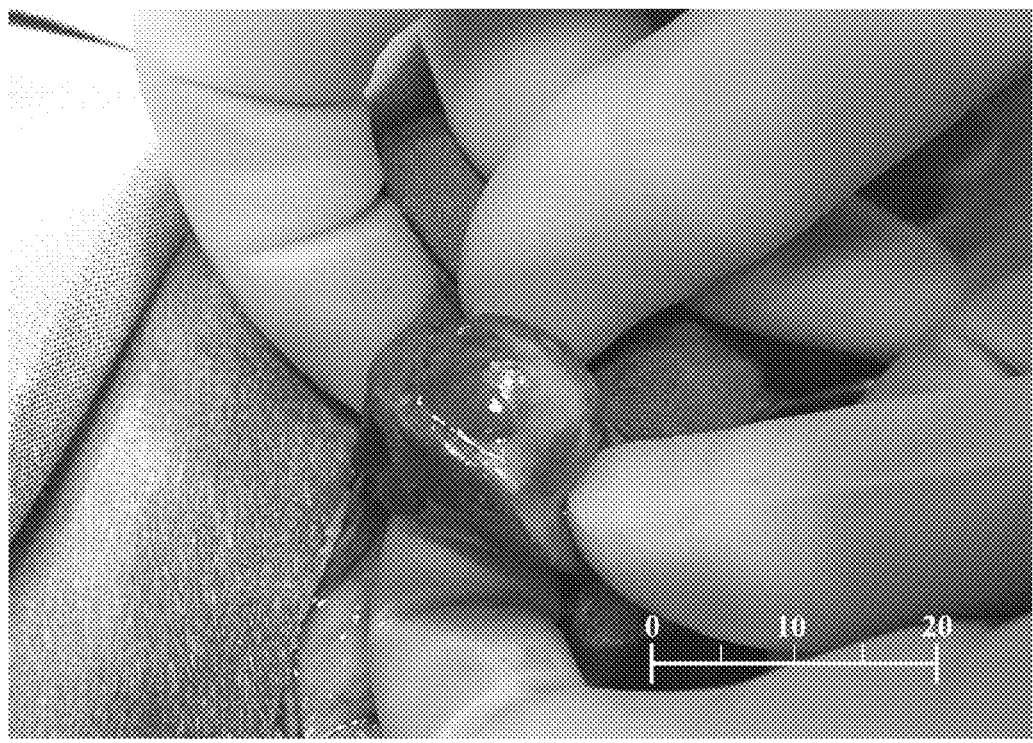
FIG. 4a-b. Picture of the tumour on the left lateral liver lobe. b) Liver overview of the rabbit. In the left lateral liver lobe (I) the tumour is implanted 10 mm from the brim of the lobe (white dot). This liver lobe which is laying on the stomach can be easily attained for implantation. Left medial lobe (II) and right medial lobe (III) are partly fused to each other and are laying on the stomach. The gall bladder is positioned on the back of the right medial lobe. The right lateral lobe (IV) is laying next to the stomach close to the backbone which is also seen on FIG. 7.
Figure 4B:
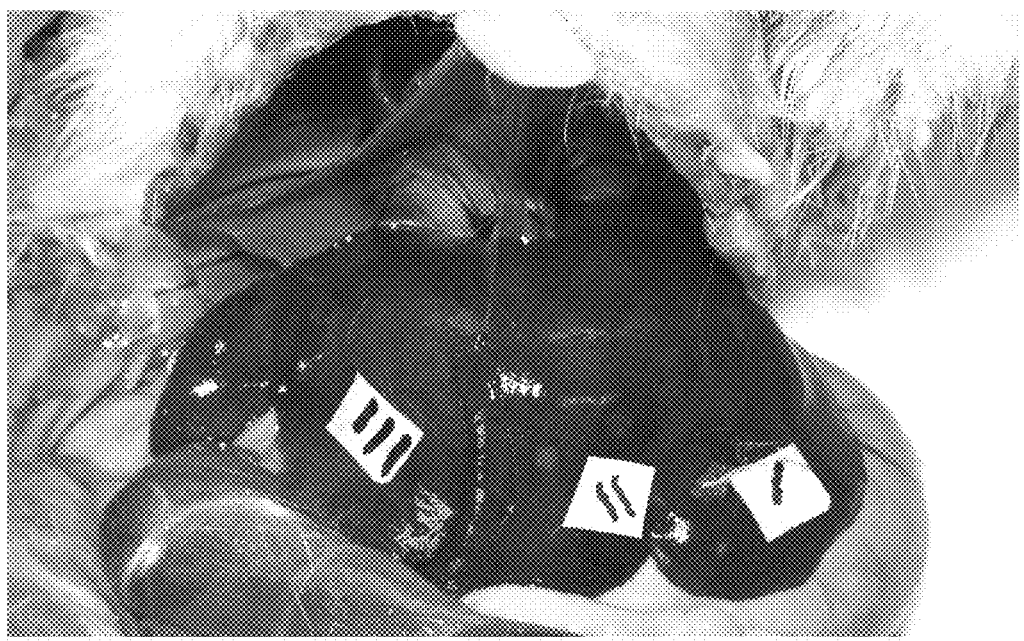
Figure 5A:
FIG. 5a-d. MR and scintigraphic images of one of the tumour-bearing rabbits. a) Schematic drawing of MR image "c" which shows the organs and tumour in the rabbit. b) Whole body scintigraphic image of the rabbit 3 days after injection of radioactive microspheres (48 mg; 560 MBq) into the hepatic artery. The small scintigraphic image in the right upper corner shows the contours of the rabbit obtained by using a "flood source". Contour of the rabbit was obtained using the "flood source". Increased accumulation of radioactivity~thus holmium loaded microspheres~is indicated with small arrows. The larger arrow indicates the activity in and around the tumour. c) T1-weighted SE image after administration of the microspheres. Field disturbances caused by holmium accumulation are seen as black areas. d) T2-weighted FFE (TE=4.6 and 9.2 msec) image after administration of the microspheres. Clearly is seen that the T2-weighted image is more sensitive for holmium as is shown by the increased black areas. Increased accumulation of holmium thus microspheres is indicated with small arrows. The larger arrow indicates the microspheres in and around the tumour.
Figure 5B:
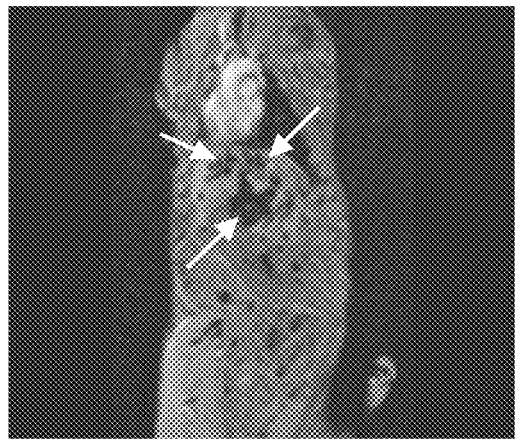
Figure 5C:
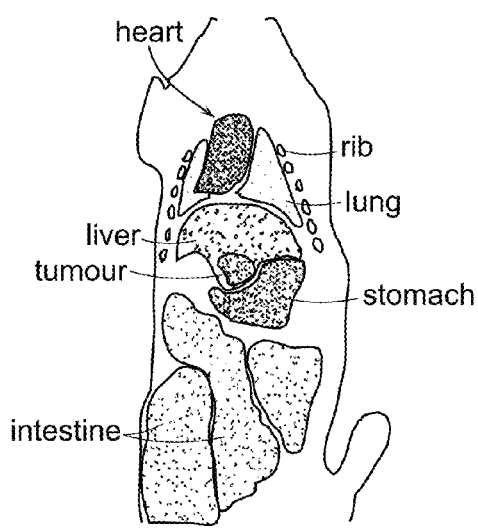
Figure 5D:
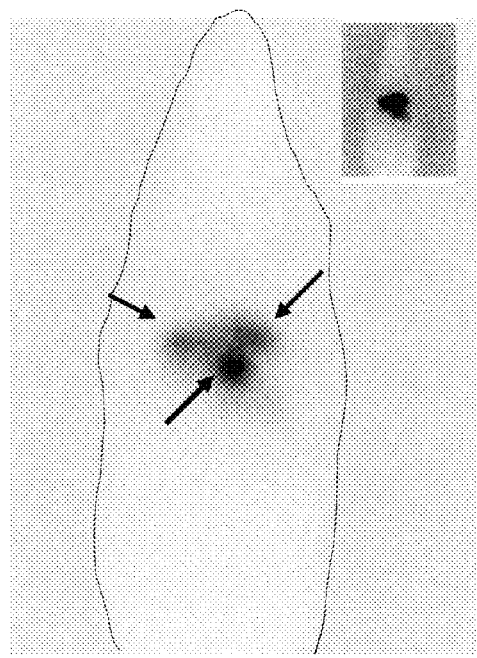

Tumour implantation and administration of $^{166}$Ho microspheres Implantation of the tumour resulted in a 100% "take"-rate. After 16 days the tumours reached a diameter of approximately 23 mm. The tumours were well vascularized as was seen with ultrasound. Tumour size varied from 10 to 17 cm$^3$ (12.7±4.1 cm$^3$) in volume measured with a ruler (FIG. 4).

Approximately 6% of the activity was adhered in the administration system after administration. An amount of 48-50 mg radioactive holmium microspheres was effectively administrated to the liver with tumour corresponding with 560-640 MBq of activity.

Biodistribution in liver tumour bearing rabbits On scintigraphic images radioactivity was especially seen in the tumour and the liver (FIG. 5). The activity in the liver was heterogeneously distributed. Increased accumulation of microspheres was seen in and around the tumour.

Figure 6A:
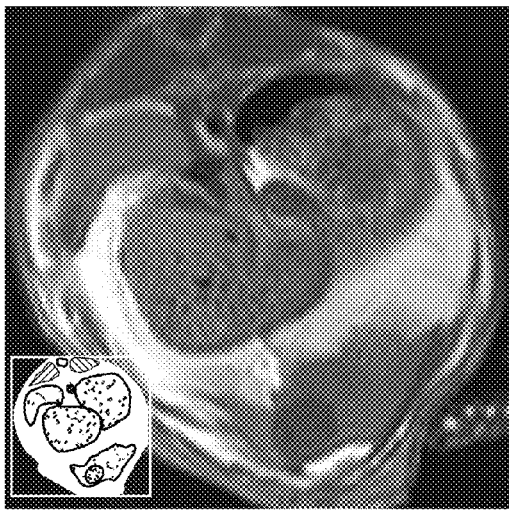
FIG. 6a-d. Magnetic resonance images of the transverse plane of the rabbit. b) Schematic drawing shows the organs which are seen in the images. The colour and position of the organs corresponds with the small drawings in each MRI image. a) Representative T1-weighted SE image before administration of the holmium loaded microspheres. c) T1-weighted SE image after administration of the microspheres. Field disturbances caused by holmium accumulation are seen as black areas indicated with small arrows. In and around the tumour indicated with the large arrow is an increased holmium accumulation seen. d) T2-weighted FFE (TE=4.6 and 9.2 msec) image after administration of the microspheres.
Figure 6B:
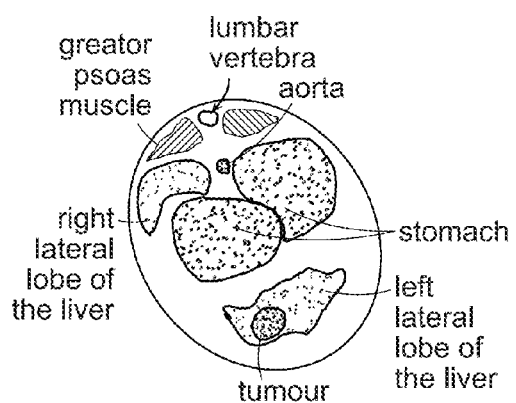
Figure 6C:
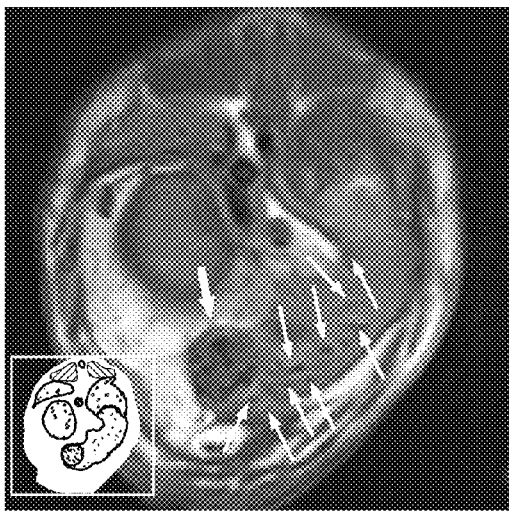
Figure 6D:
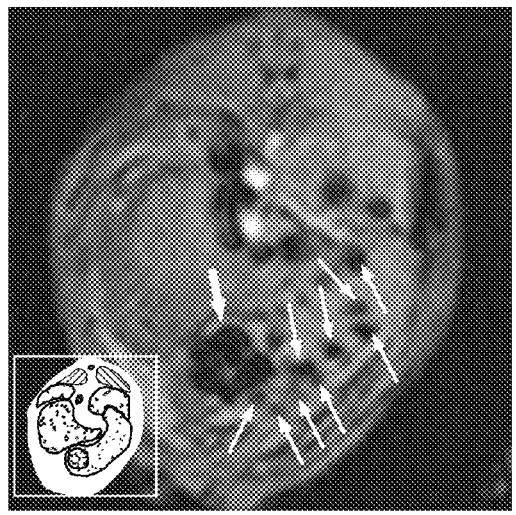
Figure 7C:
FIG. 7a-c. Magnetic resonance images of the tumour bearing rabbit liver 4 weeks after treatment. a) T1-weighted SE image. b) T2-weighted FFE image with field disturbances caused by holmium accumulation. White arrow indicate the tumour side. c) Ex-vivo liver with tumour (black arrow). The right lateral lobe is increased while the other lobes and the tumour are growth to each other.
Figure 7B:
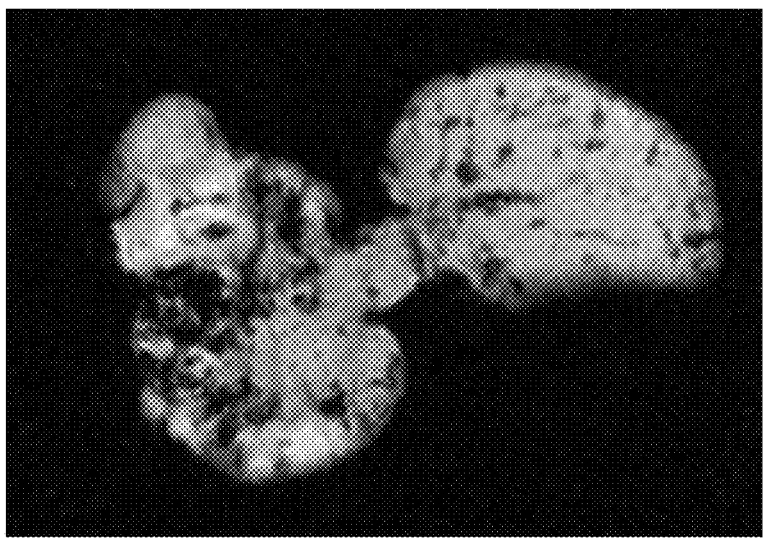
Figure 7A:
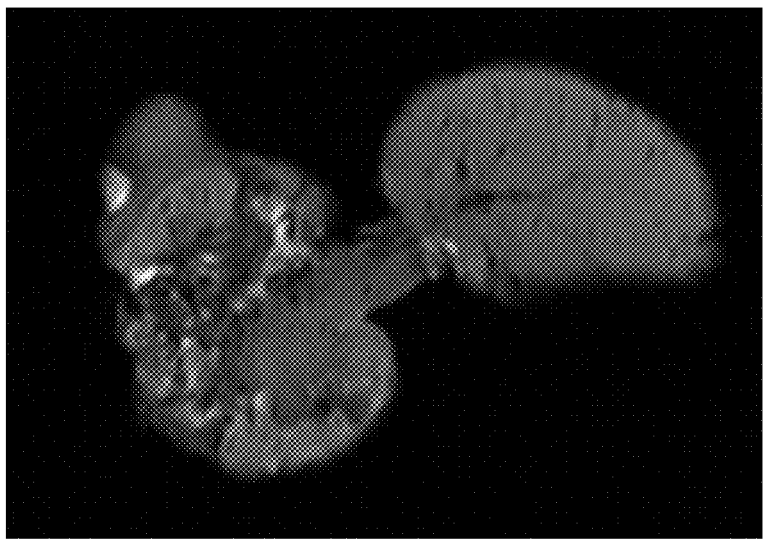
Figure 8B:
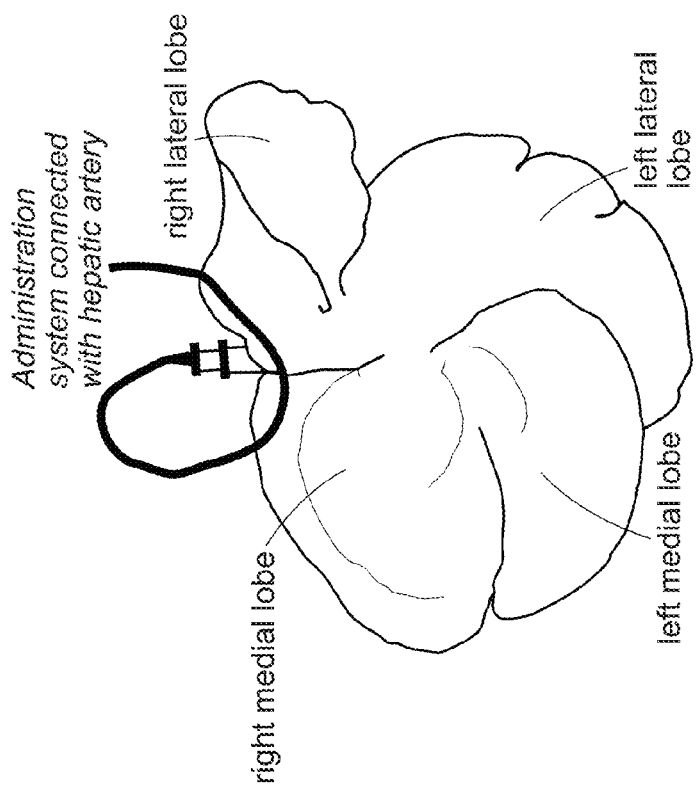
FIG. 8a-c. Dynamic magnetic resonance images (c) of the administration of holmium loaded microspheres in an ex-vivo liver (without tumour) of a rabbit (a-b). The administration was mainly selective for the medial lobes. T2* weighted FFE images shows the flow of the microspheres in the normal liver. Images 1-3 (Dyn-T2*FFE, 4 mm thickness, time resolution=5 s/slice, TE=9.2) and images 4-8 (Dyn-T2*FFE, 10 mm thickness, time resolution=1 s/slice, TE=9.2).
Figure 8A:
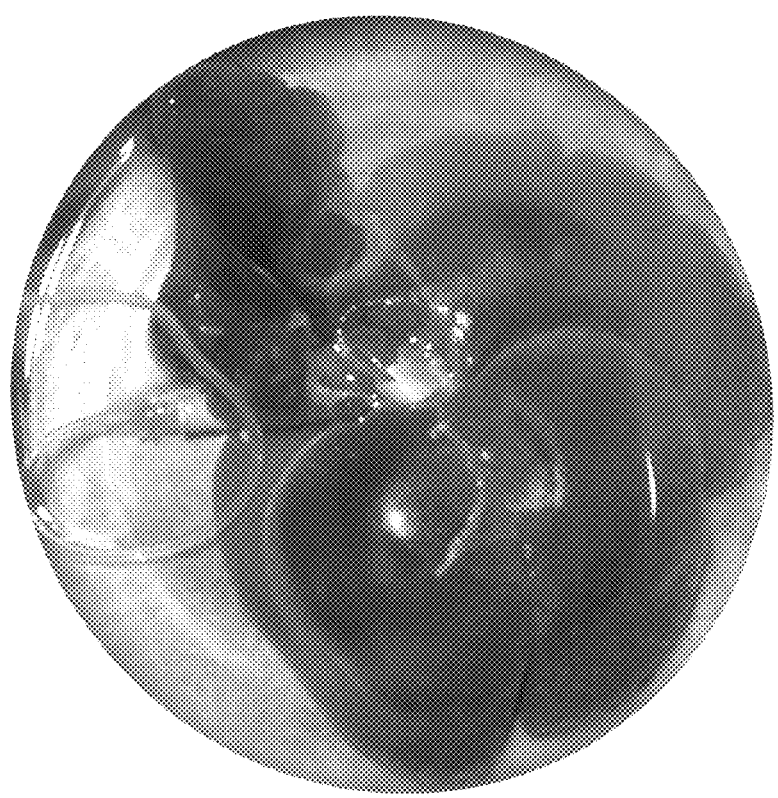
Figure 9:
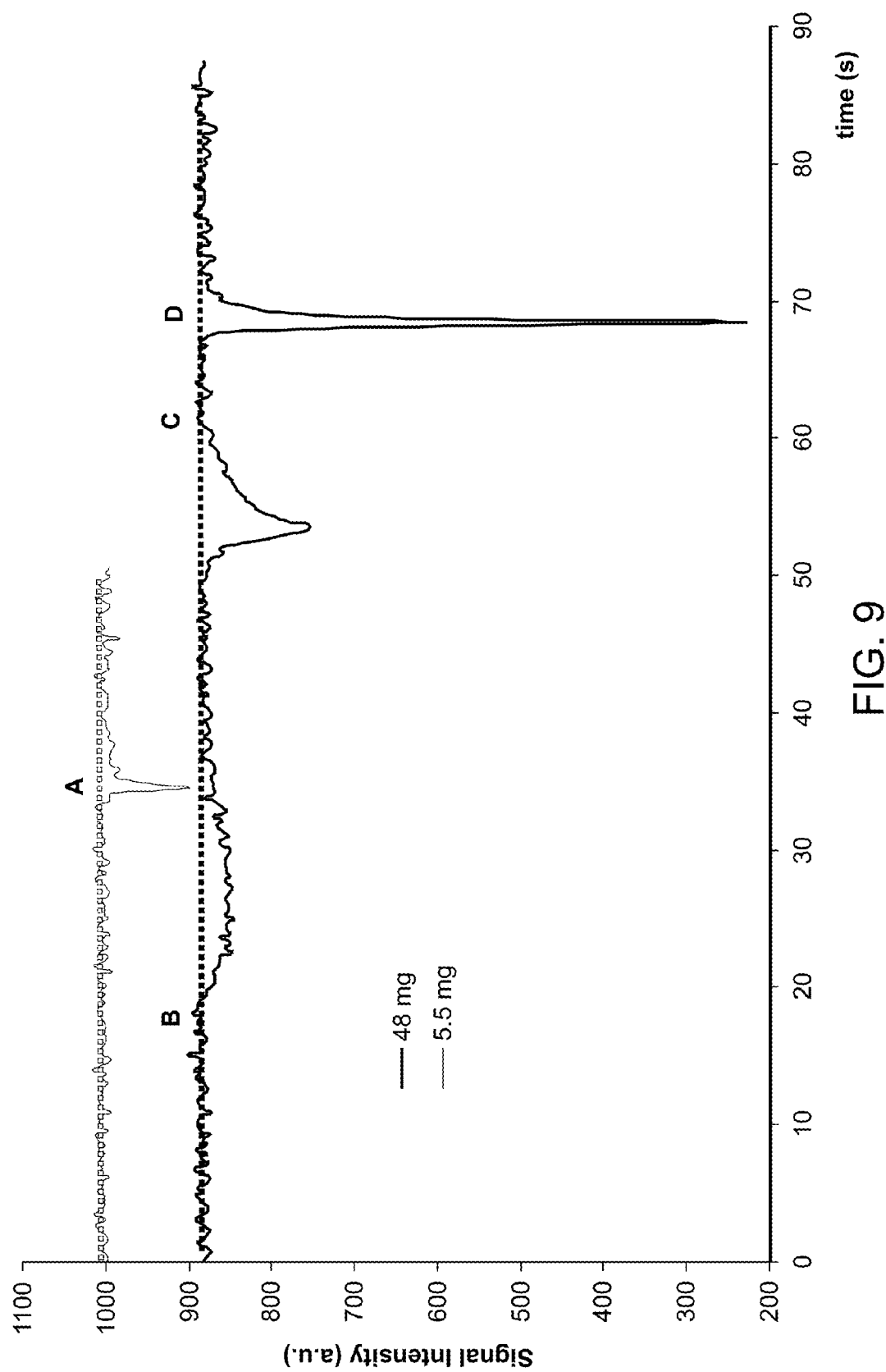
FIG. 9. Detection of holmium-loaded microspheres passing a scaled model of a human vena cava. Dashed lines denote the base line values before injection of the boluses. For the small dose (5.5 mg), a rapid injection was given at point A, whereas the large dose was injected from points B to C. Point D is a rapid flushing of the injection catheter with the circulating fluid. The areas between the base-lines and the curves are proportional to the injected doses. a.u.: arbitrary units.
Figure 8C:
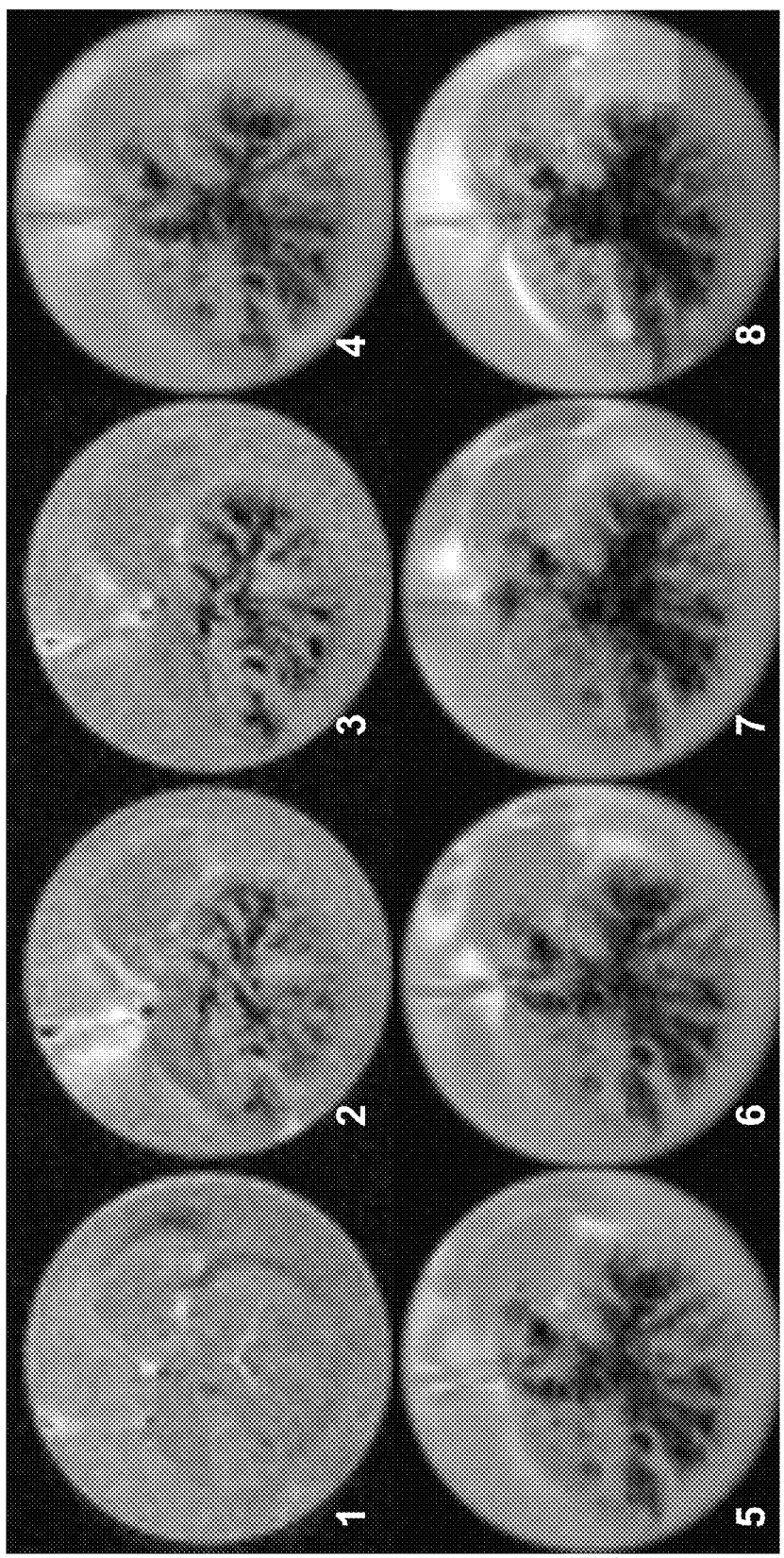

MRI of the rabbit before administration of holmium loaded microspheres resulted in an ideal diagnostic tool for the visualisation of the VX2-tumours (FIG. 6a). The tumours appear as an homogeneous, round sharply marginated lesion. On T1-weighted images the tumours are hypointense and on T2-weighted images they appear as hyperintense lesions compared with liver tissue. After administration of holmium loaded microspheres field disturbances were seen in the tumour and in the liver caused by accumulation of holmium loaded microspheres (FIG. 6b-c). The T2-weighted image is more sensitive for holmium as is shown by the increased black areas in the liver and especially around the tumour. No holmium accumulation was seen in the nucleus of the tumour.

The follow-up MR scans were obtained 17 days after administration of the microspheres. No progression was seen of the tumour. No substantial redistribution of holmium loaded microspheres was seen. In two rabbits MR images showed that the right lateral lobe was increased to 2-4 times the original volume. In the right and left medial lobe and the left lateral lobe damage of the liver tissue was observed. These lobes showed large necrotic and yellow coloured areas caused by accumulation of bile. No apparent lesions were found in the stomach and duodenum. The tumour was totally necrotic. MR images were very helpful in identifying the accumulation of the holmium loaded microspheres and thus the tumour. Histology confirmed the accumulation in and around the necrotic tumour.

Ex-vivo liver Processing of the administration of the microspheres was done in three ex-vivo rabbit livers. The accumulation in the arteries was observed by using dynamic MR. First the smaller vessels till the brim of the liver were filled with microspheres (FIG. 8c 1-4). Thereafter accumulation of the microspheres appeared in the larger blood vessels and the centre of the liver (FIG. 8c 4-8). During these experiments 0-100 mg microspheres were used. After image 5 in FIG. 8 almost no new vessels were embolised (at that moment approximately 40 mg microspheres were administered).

Discussion

In this study the feasibility of using MRI for imaging radioactive and non-radioactive holmium loaded microspheres was investigated. During in-vivo and ex-vivo experiments the biodistribution in the liver was examined, after intra-arterial administration into the hepatic artery of rabbits with implanted VX2 tumours.

Phantom experiments with holmium loaded poly(L-lactic acid) microspheres suspended in agar show a susceptibility of the HoMS which can be described by the Curie law, indicating no magnetic interactions between the Ho-ions. The magnetic susceptibility for Ho is comparable of that of Dy [17].

MR imaging is very useful to identify the anatomical structure of the abdominal region. The tumour is visible as a spherical tissue mass in the left lateral lobe. Sizes of the tumour measured with echo and with a ruler are comparable to the measurements with MRI. After administration of the radioactive holmium loaded microspheres accumulation was seen in and especially around the tumour. This can be explained by the tumour angiogenesis of liver metastases. Liver tumours have often a hypervascular brim and derive their blood supply almost exclusively from the hepatic artery [32]. Microspheres injected into the hepatic artery therefore accumulate around the tumour.

On both scintigraphic and MR images an inhomogeneous distribution of the holmium microspheres in the liver was observed. This heterogeneous distribution is described also for human patients and can explain the toleration of the liver for high doses of activity [32; 33]. Large parts of the liver will receive less activity than would be expected for a uniform distribution of activity resulting in survival of most of the liver tissue.

MR and scintigraphic images show both the holmium accumulation in the animal. However MRI combines this image with detailed information about the morphology of the animal which result in straightforward proof where in the body holmium microspheres are accumulated. It is shown that quantitative MR of holmium microspheres in a target organ with tumour provides in easy and accurate dosimetric studies.

In the ex-vivo liver experiments the feasibility of real-time MR images during administration was demonstrated. Clearly was observed that at a well-defined point no further vessels were provided of microspheres and that first the smaller vessels were filled-up with spheres. This shows that vascular tissue is limited in the capacity of gathering spheres and that administering of extra microspheres will only result in fill-up of the larger vessels. Generally, these larger vessels are non-tumour vessels and therefore will not join in tumour treatment after accumulation of spheres. The possibility of real-time controlling and changing the administration position, flow and quantity of microspheres on the basis of the MR images will result in optimalisation of therapeutic properties of radioactive holmium loaded microspheres. Customizing a treatment for each individual patient effects in better treatment resulting in decrease of liver damage and increase of the tumour to liver ratio. Tumour to liver ratio is to be understood as the ratio between the activity of and/or the number of particles in the tumour relative to the activity of and/or the number of particles in the liver. A higher ratio is therefore more effective.

Follow-up of a patient is desirable for further research and clinical explanation of observed effects. Holmium microspheres can be imaged after treatment as long as they accumulate in the body. Information about redistribution and tissue reaction on such particles can be observed with MR. The animal experiments in rabbits show that redistribution is not seen during the first 17 days.

In conclusion, this study has demonstrated that holmium loaded PLLA microspheres which can be used for internal radionuclide therapy can be imaged in-vivo. The possibility of imaging non-radioactive and radioactive holmium loaded spheres with MR opens the way for accurate administration and follow-up of a treatment.

REFERENCES

(14) Nijsen J F, Zonnenberg B A, Woittiez J R, Rook D W, Swildens-van Woudenberg I A, van Rijk P P, het Schip A D. Holmium-166 poly lactic acid microspheres applicable for intra-arterial radionuclide therapy of hepatic malignancies: effects of preparation and neutron activation techniques. Eur J Nucl Med 1999; 26(7):699-704.

(17) Fossheim S, Johansson C, Fahlvik A K, Grace D, Klaveness J. Lanthanide-based susceptibility contrast agents: assessment of the magnetic properties. Magn Reson Med 1996; 35(2):201-206.

(20) Kooijman H, Nijsen F, Spek A L, van het Schip F. Diaquatris(pentane-2,4-dionato-O,O')holmium(III) monohydrate and diaquatris(pentane-2,4-dionato-O,O') holmium(III) 4-hydroxypentan-2-one solvate dihydrate. Acta Crystallogr C 2000; 56(Pt 2):156-158.

(21) Kidd J G, Rous P. A transplantable rabbit carcinoma originating in a virus-induced papilloma and containing the virus in masked or altered form. J. Exp. Med. 71[469], 813-837. 1940. Ref Type Journal (Full)

(22) van Es R J, Franssen O, Dullens H F, Bernsen M R, Bosman F, Hennink W E, Slootweg P J. The VX2 carcinoma in the rabbit auricle as an experimental model for intra-arterial embolization of head and neck squamous cell carcinoma with dextran microspheres. Lab Anim 1999; 33(2):175-184.

(23) Herba M J, Illescas F F, Thirlwell M P, Boos G J, Rosenthall L, Atri M, Bret P M. Hepatic malignancies: improved treatment with intraarterial Y-90. Radiology 1988; 169(2):311-314.

(24) Weisskoff R M, Zuo C S, Boxerman J L, Rosen B R. Microscopic susceptibility variation and transverse relaxation: theory and experiment. Magn Reson Med 1994; 31(6):601-610.

(25) Yablonskiy D A, Haacke E M. Theory of NMR signal behavior in magnetically inhomogeneous tissues: the static dephasing regime. Magn Reson Med 1994; 32(6): 749-763.

(32) Fox R A, Klemp P F, Egan G, Mina L L, Burton M A, Gray B N. Dose distribution following selective internal radiation therapy. Int J Radiat Oncol Biol Phys 1991; 21(2):463-467.

(33) Yorke E D, Jackson A, Fox R A, Wessels B W, Gray B N. Can current models explain the lack of liver complications in Y-90 microsphere therapy? Clin Cancer Res 1999; 5(10 Suppl):3024s-3030s.

The invention claimed is:

1. A kit of parts comprising:
1) a diagnostic composition and
2) a therapeutic composition,
wherein said diagnostic composition and said therapeutic composition comprise paramagnetic poly(L)-lactic acid particles containing holmium, gadolinium and/or dysprosium acetylacetonate, wherein said particles have a diameter of at least 1 µm and wherein said therapeutic composition is more radioactive than said diagnoctic composition.

2. The kit of parts according to claim 1, wherein said diagnostic composition is non-radioactive.

3. The kit of parts according to claim 1, wherein said particles comprise holmium.

4. The kit of parts according to claim 1 wherein said particles comprise a microsphere.

5. The kit of parts according to claim 1 wherein said particles comprise a poly(L)-lactic acid microsphere.

6. A method of making a kit comprising including into the kit
1) a diagnostic composition, and
2) a therapeutic composition,
wherein said diagnostic composition and said therapeutic composition comprise paramagnetic poly(L)-lactic acid particles containing holmium, gadolinium and/or dysprosium acetylacetonate, wherein said particles have a diameter of at least 1 µm and whereby said therapeutic composition is more radioactive than said diagnostic composition.

7. The method of claim 6 wherein said particles comprises holmium.

8. The method of claim 6 wherein said particles comprise a microsphere.

9. The method of claim 6 wherein said particles comprise a poly(L)-lactic acid microsphere.

* * * * *